US00PP11501P

United States Patent [19]

Olesen et al.

[11] Patent Number: Plant 11,501

[45] Date of Patent: Sep. 5, 2000

[54] FLORIBUNDA ROSE PLANT NAMED 'POULSAIL'

[75] Inventors: L. Pernille Olesen; Mogens N. Olesen, both of Fredensborg, Denmark

[73] Assignee: Poulsen Roser ApS, Fredensborg, Denmark

[21] Appl. No.: 09/140,630

[22] Filed: Aug. 26, 1998

[51] Int. Cl.[7] ..... A01H 5/00

[52] U.S. Cl. ..... Plt./147

[58] Field of Search ..... Plt./106, 141, 147, Plt./149, 150

[56] References Cited

U.S. PATENT DOCUMENTS

P.P. 5,770 7/1986 de Ruiter ..... Plt./122

OTHER PUBLICATIONS

Cairns, ed., 1993, Modern Roses 10, The American Rose Society, Shreveport, Louisiana, p. 489.

*Primary Examiner*—Howard J. Locker

[57] ABSTRACT

A new floribunda rose plant which has abundant, non-fading, salmon-orange flowers and attractive foliage. The variety successfully propagates from softwood cuttings and is suitable for year round production in commercial glass-houses. This new and distinct variety has shown to be uniform and stable in the resulting generations from asexual propagation.

1 Drawing Sheet

SUMMARY OF THE INVENTION

The present invention constitutes a new and distinct variety of floribunda rose plant which originated from a controlled crossing between an unnamed seedling and an unnamed seedling. The two parents were crossed and the resulting seeds were planted in a controlled environment. The new variety is named 'POULsail'.

The new rose may be distinguished from its seed parent, an unnamed seedling, created by the same inventors by the following combination of characteristics:

1. The parents of the unnamed seedling are 'POULgav' Gavno and RUImired, U.S. Plant Pat. No. 5,770.

2. The unnamed seedling has bronze colored flowers, while 'POULsail' has salmon-orange flowers.

3. The unnamed seedling is slightly taller in height than 'POULsail'.

The new variety may be distinguished from its pollen parent, an unnamed seedling created by the same inventors, by the following combination of characteristics:

1. The parents of the unnamed seedling are Crimson Midinette, RUImired, U.S. Plant Pat. No. 5,770 dated Jul. 22, 1986 and POULrouge, U.S. Plant Pat. No. 9,687 dated Nov. 12, 1996.

2. The unnamed seedling is a red miniature rose and 'POULsail' is a salmon-orange floribunda.

3. The unnamed seedling has more compact growth and smaller foliage.

The objective of the hybridization of this rose variety for commercial greenhouse culture was to create a new and distinct variety with unique qualities, such as:

1. Uniform and abundant flowers;

2. Vigorous and compact growth;

3. Year-round flowering under glasshouse conditions;

4. Suitability for production from softwood curttings in pots;

5. Durable flowers and foliage which make a variety suitable for distribution in the floral industry.

This combination of qualities was not present in previously available commercial cultivars in this market class and distinguish 'POULsail' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULsail' was selected by the inventors as a single plant from the progeny of the hybridization in May, 1994.

Asexual reproduction of 'POULsail' by cuttings was first done by L. Pernille and Mogens N. Olesen in their nursery in Fredensborg, Denmark in April, 1995. This initial and other subsequent propagations conducted in controlled environments have demonstrated that the characteristics of 'POULsail' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULsail'. Specifically illustrated in SHEET 1:

1. Stem or entire plant showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a description of 'POULsail', as observed in its growth in glasshouses in Fredensborg, Denmark and Half Moon Bay, Calif., and in a field nursery in Jackson County, Oreg. Color references are made using The Royal Horticultural Society (London, England) Colour Chart, 1995, except where common terms of color are used.

For a comparison, several physical characteristics of the rose variety 'POULrouge', a patented rose variety from the same inventors described and illustrated in U.S. Plant Pat. No. 9,687 and issued on Nov. 12, 1996 are compared to 'POULsail' in Chart 1.

CHART 1

| | 'POULsail' | 'POULrouge' |
|---|---|---|
| Bud color, ¼ open | Red Group 39A–43C | Red Group 40B |
| Flower bloom color, upper petal surface | Red Group 41C | Red Group 40B |
| Flower bloom color, reverse surface | Red Group 41C | Red Group 41B |
| Leaf size | Large. 100 mm (l) × 75 mm (w) | Small. 63 mm (l) × 50 mm (w) |

Parents: Unnamed seedling×Unnamed seedling.
Classification:
*Botanical.*—*Rosa hybrida.*
*Commercial.*—Floribunda.

FLOWER AND FLOWER BUD

Blooming habit: Recurrent.
Flower bud:
*Size.*—Upon opening, 24 mm–28 mm in length from base of receptacle to end of bud.
*Bud form.*—Pointed ovoid.
*Bud color.*—Glasshouse grown plants: As sepals unfold, Red Group 39A–43C. Red Group 41B at ¼ opening.
*Nursery grown plants.*—As sepals unfold, Red Group 42A. At ¼ opening, Red Group 42A–42B.
*Sepals.*—Green Group 137C–138A. Where exposed to bright light, the reverse surface of the sepal has moderate to strong intonations of Greyed-Red Group 179A. Weak foliaceous appendages on three of the five sepals. Surfaces of sepals slightly pubescent. Limited numbers of stipitate glands on sepals with appendages.
*Receptacle.*—Surface: Smooth, glabrous. Shape: Funnel. Size: 6 (h)×7 mm (w). Color: Green Group 138A–138B.
*Peduncle.*—Surface: With few to many stipitate glands. Length: 35–50 mm average length. Color: Green Group 138B. Where exposed to bright light, the peduncle has moderate to strong intonations of Greyed-Red Group 179A. Strength: Erect.
*Borne.*—Multiple buds per stem. Generally with 2–5 buds per flowering stem.
Flower bloom:
*Size.*—Average flower diameter is 65–75 mm when open.
*Form.*—Shape of flower when viewed from the side: Upon opening, upper part: Flattened convex. Upon opening, lower part: Convex. Open flower, upper part: Flat. Open flower, lower part: Flat. Petalage: Average range: 40–45 under normal conditions with 3–5 petaloids.
Color:
*Upon opening.*—Petals: Upper Surface: Glasshouse grown plants: Red Group 40C–41B. Nursery grown plants: Red Group 42A–42B. Reverse Side: Glasshouse grown plants: Red Group 39C–41C. Nursery grown plants: Red Group 42B–42C. Basal petal spots: Outer Side: Yellow Group 1C. Inner Side: Yellow Group 4D.
*After opening.*—Outermost petals: Upper Surface: Glasshouse grown plants: Red Group 41C. Nursery grown plants: Red Group 42B–43B. Reverse Side: Glasshouse grown plants: Red Group 41C. Nursery grown plants: Red Group 42B–43B. Innermost petals: Upper Surface: Glasshouse grown plants: Red Group 41B. Nursery grown plants: Red Group 42B–43B. Reverse Side: Glasshouse grown plants: Red Group 41C–43C. Nursery grown plants: Red Group 42B–43B. Basal petal spots: Outer Side: Yellow-White Group 158B. Inner Side: Yellow-White Group 158B.
General tonality: Glasshouse grown plants: On open flower Red Group 40C. No change in the general tonality at the end of the first day. Afterwards, general tonality is Red Group 42D. Margins of center petals lighter. Nursey grown plants: On open flower Red Group 42A–43C. No change in tonality at the end of the first day. Afterwards, general tonality is Red Group 43B.
Petals:
*Petal reflex.*—Outermost petals reflex backwards. Many outermost petals are double reflexed.
*Petal edge.*—Some petals with point. Some petals notched at center.
*Petaloids.*—Present. Quantity: 3–5.
*Fragrance.*—Light floral.
*Duration.*—As a pot plant, flowers last from 8 to 10 days. As a cut flower 5 to 7 days.
*Thickness.*—Average to above thickness.
*Shape.*—Round.
*Form.*—On open blooms, innermost petals cupped somewhat.
*Arrangement.*—Imbricated.
Reproductive organs:
*Pollen.*—Color: Yellow-Orange Group 17C. Abundance: Average to above average.
*Anthers.*—Size: Medium. Color: Yellow-Orange Group 17C. Abundance: Above average.
*Filaments.*—Color: Yellow-Green Group 154C.
*Stigmas.*—Superior in location to anthers. Color: Yellow Group 4D.
*Styles.*—Color: Yellow Group 4D and Red-Purple Group 57C. Upper style area has intonation of Red-Purple Group 57C.

PLANT

Plant growth: Vigorous, compact, upright to bushy. When grown as a 15 cm pot plant, the average height of the plant itself is 25 to 30 cm and the average width is 24 to 28 cm. When grown as a nursery plant (on its own roots) the average plant height is 60–75 cm and the average plant width is 50–60 cm.
Stems:
*Color.*—Young wood: Yellow-Green Group 144B. Older wood: Yellow-Green Group 144A to Green Group 137B.
*Prickles.*—Incidence: Few. Size: Average length: 5 mm–7 mm. Some thorns smaller. Color: Green- White Group 157A with intonations of Greyed-Red Group 179C. When exposed to bright light, the thorns are almost entirely colored with intonations of Greyed-Red Group 179A. Shape: Linear to curved.

*Surface.*—Young wood: Smooth. Older wood: Smooth.

Plant foliage: Normal number of leaflets on normal leaves in middle of the stem: 5 leaflets.

*Leaf size.*—Large. 100 mm (l)×75 mm (w).

*Abundance.*—Above average.

*Color.*—Upper Leaf Surface: Green Group 137A. Lower Leaf Surface: Green Group 138B. Juvenile foliage: Upper leaf surface: Green Group 137A with moderate intonations of Greyed-Red Group 179A on margins. Where exposed to bright light, the juvenile foliage has moderate to strong intonations of Greyed-Red Group 179A. Lower leaf surface: Green Group 138B with moderate intonations of Greyed-Red Group 179A on margins and undersurface. Where exposed to bright light, the juvenile foliage, petioles and leaf rachis have moderate to strong intonations of Greyed-Red Group 179A.

Plant leaves and leaflets:

*Stipules.*—Present. Stipitate glands present on margins. Size: Small. 6 mm–8 mm. Color: Green Group 137C. Presence of hairs: Limited hairs.

*Petiole.*—Length: 22 mm–25 mm. Color: Green Group 137B. Where exposed to bright light, the petiole has moderate to strong intonations of Greyed-Red Group 179A. Margins: With limited stipitate glands. Prickles: Few to none.

*Rachis.*—Color: Green Group 137B. Where exposed to bright light, the rachis has moderate to strong intonations of Greyed-Red Group 179A. Underneath: With limited prickles. Margins: With stipitate glands.

*Leaflet.*—Edge: Serrated. Shape: Ovate.

*Other.*—Moderately glossy finish. Leathery texture.

Disease resistance: Above average resistance to mildew and Botrytis under normal growing conditions in Half Moon Bay, Calif., Jackson County, Oreg., and Fredensborg, Denmark.

We claim:

1. A new and distinct variety of rose plant of the floribunda class, substantially as herein illustrated and described as a distinct and novel rose variety due to its abundant, salmon-orange flowers, vigorous and compact growth, year round flowering under glasshouse conditions, suitability for production from softwood cuttings in pots, and durable flowers and foliage which make the variety suitable for distribution in the floral industry.

* * * * *

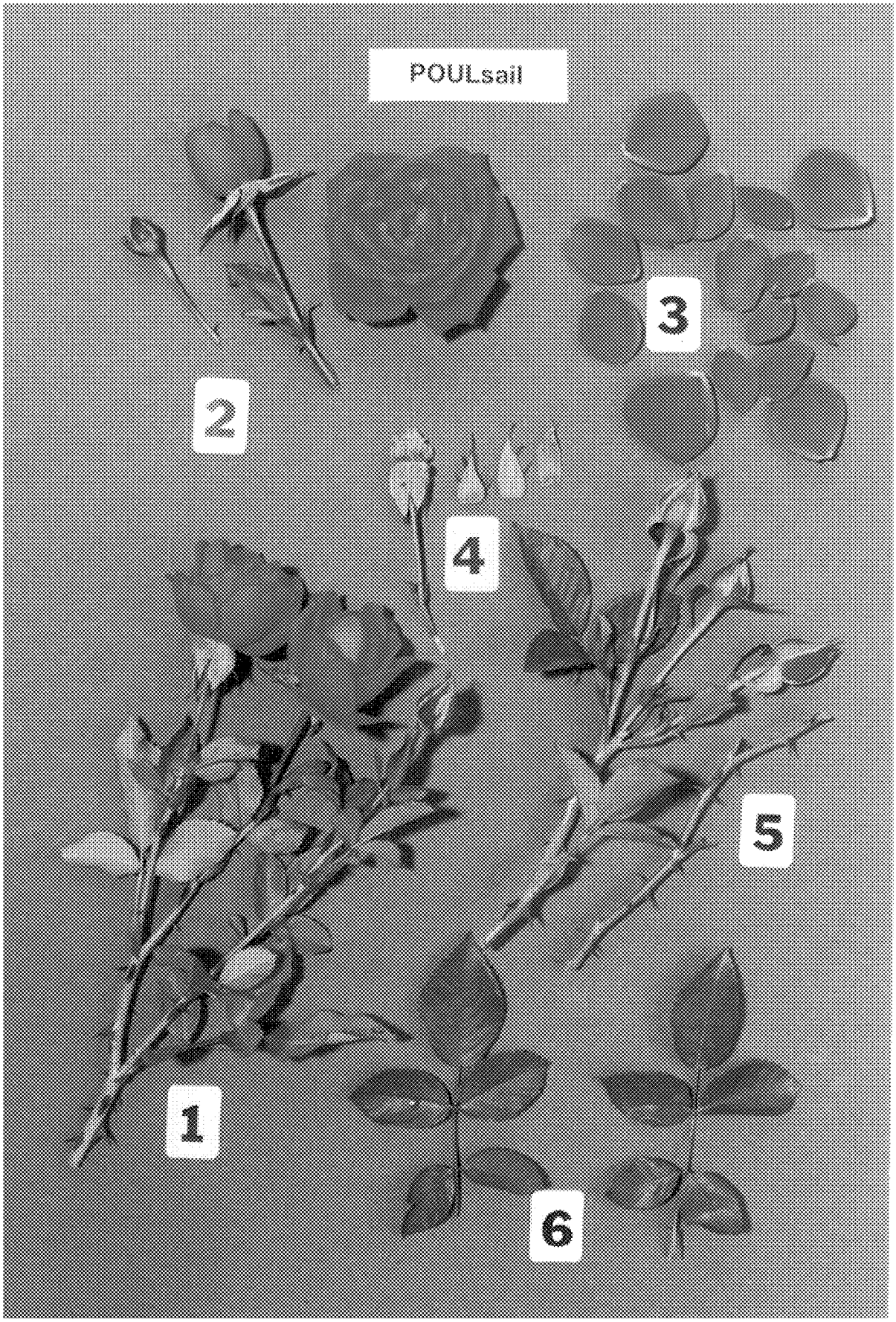
POULsail
1
2
3
4
5
6